United States Patent
Peng et al.

(10) Patent No.: US 10,472,267 B2
(45) Date of Patent: Nov. 12, 2019

(54) SALT SEPARATOR AND A METHOD FOR PRODUCING A METHANE-CONTAINING GAS MIXTURE FROM BIOMASS USING A SALT SEPARATOR

(71) Applicant: PAUL SCHERRER INSTITUT, Villigen Psi (CH)

(72) Inventors: Gaël Peng, Moutier (CH); Joachim Reimer, Wettingen (CH); Frédéric Vogel, Erlinsbach (CH); Hemma Zoehrer, Bruck am Ziller (AT); Erich De Boni, Baden (CH)

(73) Assignee: Paul Scherrer Institute, Villigen PSI (CH)

( * ) Notice: Subject to any disclaimer, the term of this patent is extended or adjusted under 35 U.S.C. 154(b) by 231 days.

(21) Appl. No.: 15/126,147

(22) PCT Filed: Mar. 2, 2015

(86) PCT No.: PCT/EP2015/054313
§ 371 (c)(1),
(2) Date: Sep. 14, 2016

(87) PCT Pub. No.: WO2015/135785
PCT Pub. Date: Sep. 17, 2015

(65) Prior Publication Data
US 2017/0081229 A1    Mar. 23, 2017

(30) Foreign Application Priority Data
Mar. 14, 2014    (EP) ..................... 14159871

(51) Int. Cl.
*C02F 11/08*    (2006.01)
*C02F 1/02*    (2006.01)
(Continued)

(52) U.S. Cl.
CPC .............. *C02F 11/086* (2013.01); *C02F 1/02* (2013.01); *C02F 1/025* (2013.01); *C02F 1/52* (2013.01);
(Continued)

(58) Field of Classification Search
CPC .......... C02F 11/086; C02F 1/025; C02F 1/52; C02F 1/02; C02F 11/04; C02F 2103/26;
(Continued)

(56) References Cited

U.S. PATENT DOCUMENTS 4,155,848 A * 5/1979 Sato ....................... B01J 19/246
                                                    162/31
4,221,763 A * 9/1980 Greene ...................... B01J 3/04
                                                   165/158
(Continued)

FOREIGN PATENT DOCUMENTS

BE    1018840 A3    9/2011
DE    29913370 U1    9/1999
(Continued)

OTHER PUBLICATIONS

Vogel, F., et al. "Hydrothermal Gasification of Woody Biomass". Catalytic Process Engineering—LEM—Laboratory for Energy and Materials Cycles. Chem. Eng. Trans., 2: 771-777.
(Continued)

*Primary Examiner* — David C Mellon
(74) *Attorney, Agent, or Firm* — Laurence A. Greenberg; Werner H. Stemer; Ralph E. Locher

(57) ABSTRACT

A salt separator separates salts and/or solid materials from a pumpable aqueous fluid mixture under process conditions, which lie in the range of the critical point for the fluid mixture. The salt separator contains a reaction zone in a cavity for transforming the pumpable aqueous fluid mixture into a raw mixture, e.g. a methanation reaction, and a feed
(Continued)

opening for the pumpable aqueous fluid mixture to the cavity. The feed opening is realized in a rising pipe that protrudes into the cavity. A first extraction opening is provided for the raw mixture freed of salts and/or solid materials. The first extraction opening is arranged in the upper region of the cavity and a second extraction opening is provided for a brine containing the salt and/or the solid materials. The second extraction opening is arranged in the lower region of the cavity and is located lower down than the feed opening.

7 Claims, 2 Drawing Sheets

(51) Int. Cl.
  *C02F 11/04* (2006.01)
  *C02F 1/52* (2006.01)
  *C07C 1/20* (2006.01)
  *C02F 101/10* (2006.01)
  *C02F 103/26* (2006.01)

(52) U.S. Cl.
  CPC ............... *C02F 11/04* (2013.01); *C07C 1/20* (2013.01); *C02F 2001/5218* (2013.01); *C02F 2101/10* (2013.01); *C02F 2103/26* (2013.01); *C02F 2201/002* (2013.01); *C02F 2209/02* (2013.01); *C12P 2201/00* (2013.01); *Y02E 50/14* (2013.01); *Y02E 50/343* (2013.01)

(58) Field of Classification Search
  CPC .......... C02F 2101/10; C02F 2001/5218; C02F 2209/02; C02F 2201/002; C07C 1/20; Y02E 50/14; Y02E 50/343; C12P 2201/00
  See application file for complete search history.

(56) References Cited

U.S. PATENT DOCUMENTS

| | | | | |
|---|---|---|---|---|
| 4,229,296 A * | 10/1980 | Wheaton | ................ | B01J 3/04 210/104 |
| 4,822,497 A * | 4/1989 | Hong | ................ | B01D 11/0203 210/177 |
| 5,200,093 A * | 4/1993 | Barner | ................ | C02F 11/086 210/761 |
| 5,461,648 A * | 10/1995 | Nauflett | ................ | B01J 3/008 210/177 |
| 5,552,039 A * | 9/1996 | McBrayer, Jr. | ................ | B01J 3/042 210/177 |
| 5,707,417 A | 1/1998 | Yokoyama et al. | | |
| 6,214,222 B1 * | 4/2001 | Gerber | ................ | B01J 19/10 204/666 |
| 6,238,568 B1 * | 5/2001 | Hazlebeck | ................ | A62D 3/20 210/697 |
| 6,475,396 B1 * | 11/2002 | Wofford, III | ................ | B01J 19/26 210/198.1 |
| 7,611,625 B2 * | 11/2009 | Hazlebeck | ................ | C02F 11/086 210/179 |
| 8,475,549 B2 | 7/2013 | Vogel et al. | | |
| 9,950,939 B2 * | 4/2018 | Trembly | ................ | B01J 3/008 |
| 2004/0195160 A1 * | 10/2004 | Max | ................ | A23L 2/08 210/177 |
| 2013/0126442 A1 * | 5/2013 | Bakas | ................ | C02F 1/725 210/758 |
| 2014/0154767 A1 | 6/2014 | O'Regan | | |

FOREIGN PATENT DOCUMENTS

| | | | | |
|---|---|---|---|---|
| DE | 20220307 U1 | 4/2003 | | |
| DE | 10217165 A1 | 2/2004 | | |
| EP | 1772202 A1 | 4/2007 | | |
| WO | 2011154226 A1 | 12/2011 | | |
| WO | 2013005202 A1 | 1/2013 | | |
| WO | WO-2013112654 A1 * | 8/2013 | ............. | B01J 3/008 |

OTHER PUBLICATIONS

Yoshida. H., et al.: "Efficient, high-speed methane fermentation for sewage sludge using subcritical water hydrolysis as pretreatment", Bioresource Technology, Elsevier BV, GB, Bd. 100, Nr. 12, Jun. 1, 2009 (Jun. 1, 2009), Seiten 2933-2939.

Scheurer, K., et al.: "Biogene Güter in der Schweiz Massen—und Energieflüsse" . Hochschule Wädenswil, (HSW) 8820 Wädenswil Feb. 2001; (English Abstract on p. 6).

* cited by examiner

Salts: 0.1 mol/l $Na_2SO_4$ + 0.05 mol/l $K_2SO_4$ (Type 2)
Fluid: 10 wt.% IPA in water
$T_{sp}$ = 450°C, p = 300 bar

SALT SEPARATOR AND A METHOD FOR PRODUCING A METHANE-CONTAINING GAS MIXTURE FROM BIOMASS USING A SALT SEPARATOR

BACKGROUND OF THE INVENTION

Field of the Invention

The present invention relates to a salt separator and a method for producing a methane-containing gas mixture from biomass using a salt separator.

The term "biomass" is understood to mean plant or vegetable matter. For example, wood, dung, manure, straw, grass, algae, sludge and offal may be given as examples. However, the present method is also suitable for other materials with organic components such as, for example, plastic waste, waste water, sweepings, used tires, waste paper, waste oils, organic solvents, fossil biomass (peat, coal, crude oil). In general terms, the salt separator is suitable for the separation of salt from aqueous solutions with and without organic matter.

In a study by ZHAW Wädenswil commissioned by the Swiss Federal Office of Energy (FOE, Switzerland), "Scheurer, K.; Baier, U. Biogene Güter in der Schweiz. Massen- and Energieflüsse. [Biogenic goods in Switzerland. Mass and energy flow.] Hochschule Wädenswil, im Auftrag des BFE, Programm Biomasse, Schlussbericht, February 2001", the major, largely unused energy potential of manure is indicated. The total farmyard manure (dung+manure) in 1998/99 amounted to 2.283 million tonnes DM (dry matter), equivalent to an energy content of 37 PJ. In 1998 the fermentation of 4,700 tonnes DM of farmyard manure produced approximately 48 TJ of energy in the form of biogas, which is only approx. 0.1% of the total energy potential of farmyard manure. With fermentation, large quantities of non-fermentable solid materials also accrue. Woody biomass is practically impossible to ferment.

Hereinafter the term "hydrothermal" means an aqueous system under increased pressure and at a raised temperature, typically close to or above the critical point of water (374° C., 221 bar). Near-critical and super critical water form an interesting reaction medium for the performance of chemical reactions. This medium is particularly suitable for hydrolysis and the conversion of biomass to liquid and gaseous products. As the transition of a pressurized liquid system to a super critical state does not constitute a genuine phase transition, evaporation enthalpy need not be used for the water contained in the biomass, in contrast to the gas phase processes (e.g. atmospheric gasification of wet biomass). Therefore hydrothermal processes have the potential for high thermal efficiencies.

The preferred reaction for the conversion of biomass to methane may be described with the following stoichiometry using wood as an example:

$$CH_{1.52}O_{0.64}(s) + 0.3 H_2O(g) \rightarrow 0.53 CH_4(g) + 0.47 CO_2(g) \quad (1)$$

Under normal conditions (low water-partial pressure), biomass is not, or not fully, converted according to eq. (1) with water but by-products such as, for example, tars or fixed carbon (coke) are produced. If it is possible to select the reaction conditions such that the reaction (1) is completed in full, high thermal efficiency can be expected as the reaction (1) is mildly exothermic. Theoretically, the maximum possible efficiency is 95% (based on the lower calorific value $H_u$ of the wood). A system analysis for a commercial process performed by the applicant revealed achievable efficiency in the range of 70-80% for wood. This was described in detail in the reference "Vogel, F., and F. Hildebrand, Catalytic Hydrothermal Gasification of Woody Biomass at High Feed Concentrations. Chem. Eng. Trans. 2, 2002, 771-777". This is significantly higher than the efficiency of other methods for the conversion of wood to methane. In short, however, the processes currently known for methane production from biomass continue to fall short of theoretical expectations in terms of achievable efficiencies, making their use economically unviable at present.

To improve the efficiency of a hydrothermal process for methane production, in the European patent application EP 1 772 202 A1 a method for producing methane from biomass is disclosed which has the following steps:

a) A biomass slurry is produced from the biomass by adjusting the optimum dry matter content,
b) The biomass slurry is pressurized,
c) The pressurized biomass slurry is heated to liquefy the solid organic components of the biomass slurry,
d) The biomass slurry thus pressurized and heated is further heated to at least the critical temperature of the mixture itself,
e) Pressurized and at a higher temperature, precipitated solid materials from the fluid phase are separated in the process, and
f) At least part of the fluid phase, pressurized and at a higher temperature, is gasified to form a methane-rich gas by means of a catalytic reactor.

In this way, a highly efficient method was created because the majority of the materials disrupting catalytic gasification, in particular, salts, can be separated from the mixture by means of precipitation under super critical conditions. In this way, a high yield of methane and a high reaction rate with a simultaneously long service life of the catalytic converter can be achieved for catalytic gasification.

Extensive papers in the literature show that salt separation in this hydrothermal process is of major importance for the achievable efficiency of the overall process and for the achievable service life of the methanation catalytic converter. Nevertheless, the disadvantage of all previously known salt separators is that salt separation is still not satisfactory or, although satisfactory, necessitates higher thermodynamic or mechanical engineering outlay. In addition, clogging and deposits are a major problem in such salt separators. In particular, it has been shown that particularly in the case of Super Critical Water Oxidation, well-known salt separators do not work well.

BRIEF SUMMARY OF THE INVENTION

Based on the prior art, the task of the invention is therefore to specify a salt separator and a method for the hydrothermal generation of a methane-containing gas from biomass using a salt separator, wherein the design and operation of the salt separator should be simple and wherein the method should be particularly efficient.

This object is achieved according to the invention with regard to the salt separator by a salt separator for separating salts and/or solid materials from a pumpable aqueous fluid mixture under process conditions which preferably lie substantially in the range of the critical point for water, wherein the salt separator comprises the following components:

a) A reaction zone in the form of a cavity for transforming the pumpable aqueous fluid mixture into a raw mixture for subsequent further processing, e.g. a methanation reaction;

b) A feed opening for the pumpable aqueous fluid mixture to the cavity, wherein the feed opening is realized in a rising pipe that protrudes into the cavity;
c) A first extraction opening for the raw mixture freed of salt and/or solid materials, wherein the first extraction opening is arranged in the upper region of the cavity; and
d) A second extraction opening for a brine comprising the salt and/or the solid materials, wherein the second extraction opening is arranged in the lower region of the cavity and is located lower down than the feed opening.

Surprisingly, upon entry of the pumpable aqueous fluid mixture, this salt separator makes it possible to separate the salts and/or solid materials contained therein and remove them from the ongoing process stream with previously unknown efficiency. Suitable fluid mixtures here, for example, are a pumpable biomass slurry, geothermal effluents, effluent from oil wells and generally, all types of saline process waters. For example, with a salt separator of this design it is possible to separate a mixture of 100 millimolar sodium sulfate and 50 millimolar potassium sulfate without clogging, which with the previously known salt separators regularly led to a solid deposit and consequently to an accumulation of salt, which can clog the salt separator.

In an advantageous embodiment of the present invention it may be provided that the cavity is cylindrical in design and can essentially be vertically aligned, wherein the alignment in a vertical direction is greater than the diameter of the cavity. The cavity is therefore in the shape of a rising column in which the raw mixture increasingly freed of salt can rise and be separated in the subsequent handling process. Typically, it is then also expedient if the first extraction opening is arranged in the region of the highest point of the cavity.

Accordingly, it is also expedient if the second extraction opening is arranged in the region of the lowest point of the cavity. Separation of the brine comprising the salt and/or the solid materials can then take place laterally, enabling the pumpable aqueous fluid mixture to be fed vertically into the cavity directly from below. In a further expedient embodiment of the present invention it may then also be provided that the feed opening is located on the cavity-sided end of a rising pipe which protrudes vertically into the cavity. In this way, a sufficiently large spatial separation of the feed opening and the second extraction opening is thus produced, which results in a sump above the second extraction opening.

In order to be able to adhere to the process conditions, which should lie substantially in the range of and preferably above the pseudocritical point for the respective fluid mixture particularly well, it may be provided that the cavity can be heated. Thus, for example, electrical resistance heating elements and/or also induction heating elements arranged on the walls of the cavity can be provided. Heating of the external wall by means of hot gases such as, for example, exhaust gases from firing or process off-gases, is also possible. Furthermore, it is possible to achieve the required heating by adding oxidizing agents to the entering fluid, e.g. nitrates, oxygen or hydrogen peroxide.

With regard to the method, the aforementioned task is achieved according to the invention by a method for generating a methane-containing gas mixture from biomass in which salt and/or solid materials are extracted from a pumpable aqueous biomass slurry before the methanation reaction in a salt separator.

BRIEF DESCRIPTION OF THE SEVERAL VIEWS OF THE DRAWING

Advantageous embodiments of the present invention are explained in more detail hereinafter with reference to the diagram for the salt separator and the method performed in exemplary fashion therewith for the gasification of biomass (e.g. wood or manure-solid materials). The figures show.

DESCRIPTION OF THE INVENTION

Figure 1:
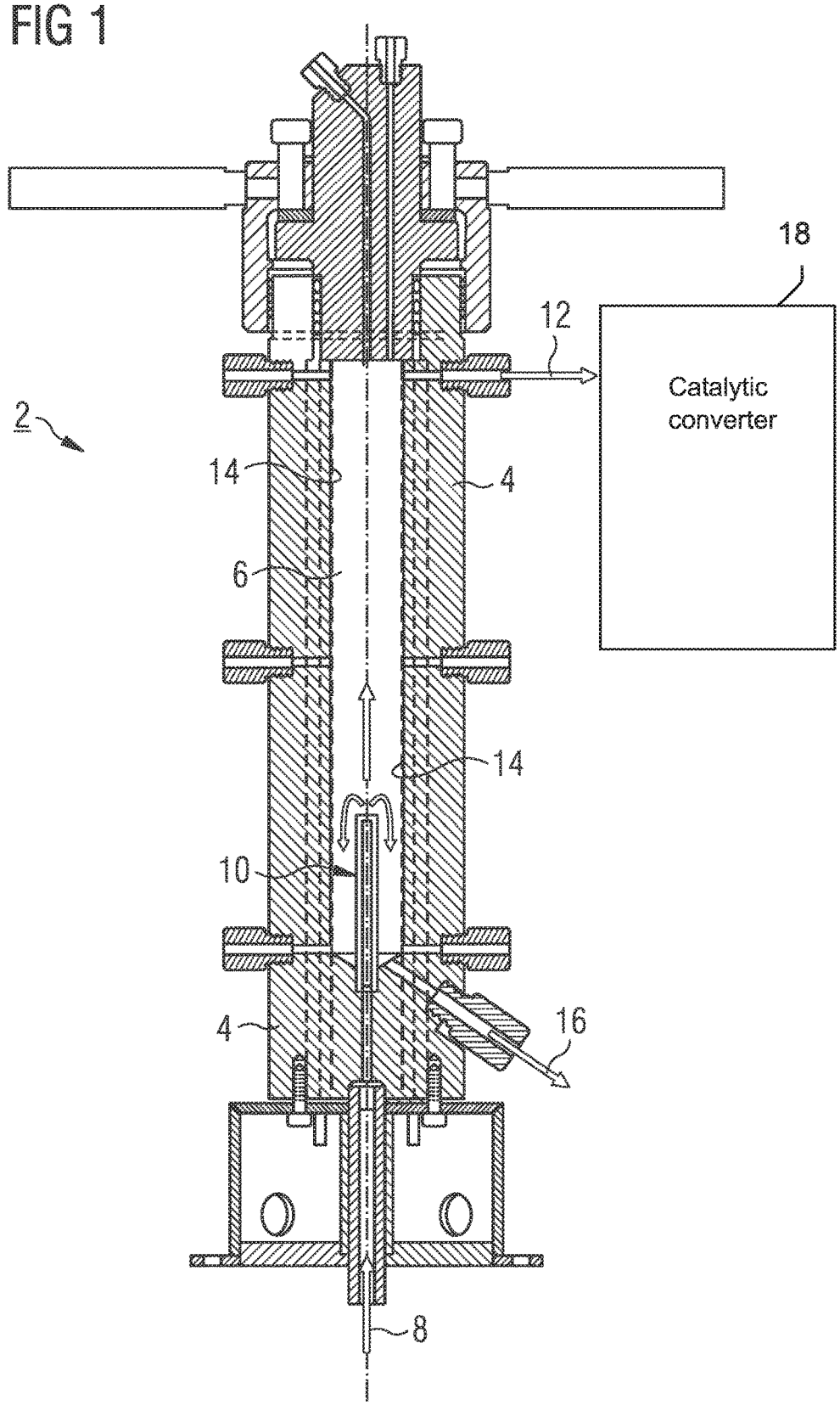
FIG. 1 A diagrammatic view of a longitudinal section through a salt separator.

FIG. 1 shows a diagrammatic view of a longitudinal section through a salt separator 2, as used for separating salts and/or solid materials from an aqueous fluid mixture. The raw product freed of salts and/or solid materials then undergoes further processing, e.g. a methanation reaction, wherein due to the eliminated salt and/or solid material content, a high level of selectivity and long service life of any catalytic converters 18 employed and a low level of corrosion of the surface subjected to the process can be achieved.

The salt separator 2 typically comprises a stainless steel case 4 (or another suitable material such as titanium or a nickel alloy) which encloses a cylindrical cavity 6. In this sense, the cavity 6 is a reaction chamber in which salts dissolved in the aqueous fluid mixture can be extracted under the thermodynamic conditions prevailing in the cavity 6, which essentially correspond to the critical point for the fluid mixture. In the lower region of the cavity 6 a supply 8 is provided through which the aqueous fluid mixture is fed into the cavity 6 under high pressure of 200 to 400 bar at a temperature of approximately 350 to 500° C. In the process, the aqueous fluid mixture is released into the cavity 6 from a rising pipe 10. Essentially, at the highest position in the cavity 6 a first extraction opening 12 for a raw fluid largely freed of salts and/or solid materials which can then be introduced to the actual further processing, e.g. a methanation reaction, while achieving the aforementioned advantages. Essentially, at the lowest position in the cavity 6 a second extraction opening 16 for a brine comprising the salt and/or solid materials is provided which is thereby extracted from the further handling process. To maintain the high temperatures in the cavity 6, heating elements 14 in the form of resistance and/or induction heating elements arranged on the walls of the cavity are provided. However, alternatively or in addition, heating of the external wall by means of hot gases such as, for example, exhaust gases from firing or process off-gases, is also possible. Furthermore, it is possible to achieve the required heating by adding oxidizing agents to the entering fluid, e.g. nitrates, oxygen or hydrogen peroxide.

It comes as a complete surprise that the introduction of the aqueous fluid mixture from below into the salt separator 2 had the pleasing result of extensively separating salts and/or solids from the raw fluid then intended for further processing.

Figure 2:
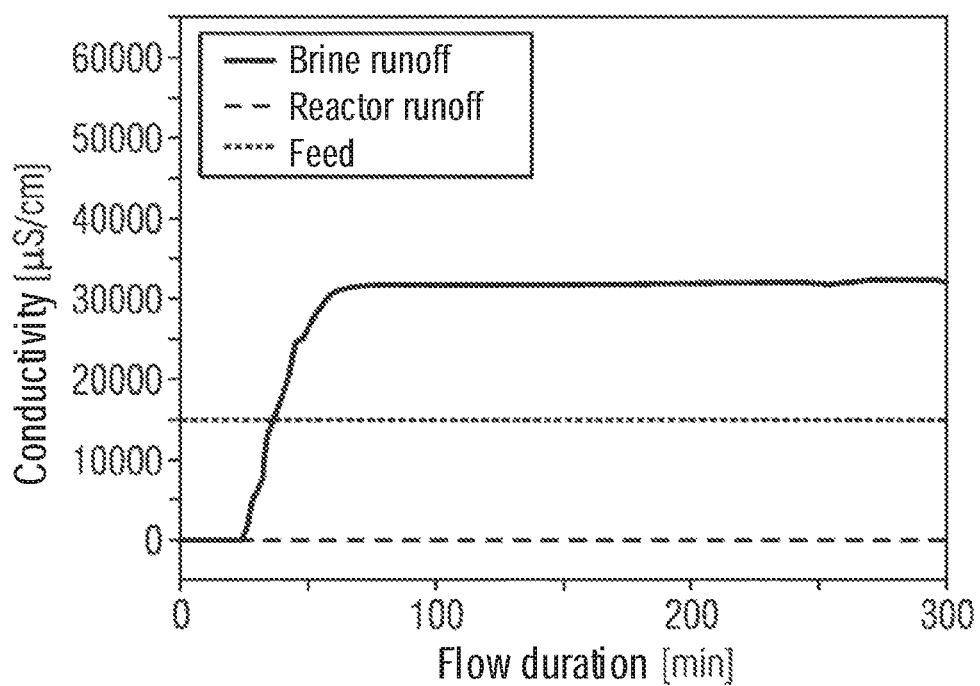
FIG. 2 A chronological sequence of the specific conductivity of a reactant of 10 wt % iso-propanol in water with a salt loading of 0.1 mol/l sodium sulfate and 0.05 mol/l potassium sulfate in a salt separator in accordance with FIG. 1 at a temperature of 450° C. and a pressure of 300 bar.

By way of example, FIG. 2 also shows a chronological sequence of the specific conductivity of a reactant of 10 wt % iso-propanol in water with a salt loading of 0.1 mol/l sodium sulfate and 0.05 mol/l potassium sulfate in a salt separator 2 in accordance with FIG. 1 at a temperature of 450° C. and a pressure of 300 bar. Iso-propanol was consciously selected at this point as it is good at emulating the organic matter of a liquefied biomass slurry which plays a role in the separation of salts. As shown in the figure, the conductivity of the brine increases very rapidly to approximately 30 mS/cm. At the same time, the conductivity of the "cleaned" raw fluid is close to zero, indicating the complete separation of the sulfates causing the conductivity from the raw fluid.

With regard to the aforementioned European patent application EP 1 772 202 A1, the method for methane production should also be briefly described again:

The biomass is conditioned in a 1st procedural step, i.e. crushed and reduced to the desired proportion of dry matter (DM), preferably by means of wet grinding. This results in a pumpable slurry. To improve pumpability, other additives can be added to the biomass (e.g. starch, waste oils). The desired proportion of dry matter is a mass fraction of 5 to 80, preferably a mass fraction of approximately 15 to 40. The method operates particularly economically if the proportion of organic dry matter is a mass fraction of approximately 20 or more.

The conditioned biomass slurry is put under high pressure (200-400 bar) in a 2nd procedural step and conveyed continuously or intermittently. Extruders, high pressure eccentric screw pumps, piston diaphragm pumps, and solid material pumps are particularly suitable as conveyors.

In a 3rd procedural step the biomass slurry is heated under pressure to 200-350° C. The solid organic biomass components are largely liquefied in the process. For better heating and liquefaction, this process stage may include static mixing elements and/or a catalytic converter (e.g. zinc oxide).

In a 4th procedural step the pressurized, heated and liquefied biomass slurry in the salt separator 2 is quickly heated to a higher temperature, preferably in the range of or above the critical temperature of the respective mixture. The critical temperature of water at 374° C. and 221 bar serves as a reference point here. This can take place by means of external heat input (e.g. by means of a burner/catalytic burner which is supplied with recycled product gas) or by adding suitable oxidizing agents (e.g. oxygen, air, hydrogen peroxide, ammonium- and other nitrates) directly in the 4th procedural stage (or one of the preceding process steps 1-3). As a result, most of the salts and remaining solid materials are precipitated and can be collected. The collected precipitates are constantly or periodically removed from the process by way of the second extraction opening 16. The separation and recovery of solid materials as salts in front of the catalytic gasification reactor under hydrothermal conditions and the possible addition of saline oxidizing agents (nitrates, e.g. ammonium nitrate) for partial oxidation of the biomass under hydrothermal conditions improve performance and increase the efficiency of the method substantially. Due to the properties of the source materials, the extracted solid materials are very rich in nitrogen, phosphoric and potassium salts and are therefore particularly suitable for reuse as fertilizers, for example, for agriculture or for algae culture.

In a 5th procedural step the hot biofuel (the hot raw fluid), now freed from most of the solid materials, arrives at a reactor fitted with a suitable catalytic converter where gasification to methane, carbon dioxide, hydrogen and traces of carbon monoxide and higher hydrocarbons (ethane, propane) takes place. The catalytic converter preferably comprises ruthenium and in addition may also contain nickel (e.g. Raney® nickel) as well as proportions of chrome and/or copper. Other catalytic converters based on Ni, Re, or Rh as the active metal can also be used. The reactor is preferably designed as a fluidized bed reactor, as a monolith reactor or as wall reactor (a tube or tube assembly coated with a catalytic converter). However, tubes could also be used in which catalytically coated sheets of metal are used.

In a 6th procedural step the methane-rich product flow is then put to further use. This procedural step can also be used to separate methane from CO2 and the remaining gas components. The product flow can also be cooled to approx. 50° C. and the gas phase separated from the liquid phase under pressure. In a suitable device (e.g. acid scrubbing tower, membrane separation, adsorber) the methane can be separated from the other components from the gas phase and is then available under high pressure (approx. 200 to 400 bar). This results in the omission of a compression step to fill gas cylinders with the methane, to offer it as fuel at a gas service station or to feed it into the gas network. The direct use of the compressed gas as fuel in a gas turbine process is also conceivable.

Hereafter the supply of methane from biomass, among other things for natural gas service stations and/or for feeding into the gas network, for filling in cylinders, or use as fuel in pressure suitable for gas turbines provides strong economic value.

Even if the description of a method for obtaining methane from biomass is paramount here, the salt separator according to the invention can also be used in a method for cleaning other aqueous fluid mixtures. Suitable fluid mixtures are, for example, a pumpable biomass slurry, geothermal effluents, effluent from oil wells and generally, all types of saline process waters, with and without organic matter.

The invention claimed is:

1. A combination, comprising:
   a salt separator for separating at least one of salts or solid materials from a pumpable aqueous fluid mixture under process conditions; and
   a catalytic converter configured for performing a methanation reaction;
   the salt separator including:
   a case with walls defining a reaction zone in a form of a cavity for transforming the pumpable aqueous fluid mixture into a raw mixture for further processing, said case having a bottom;
   a rising pipe having a feed opening for feeding the pumpable aqueous fluid mixture to said cavity, said rising pipe protruding through said bottom of said case and into said cavity such that said feed opening is displaced away from said bottom of said case;
   said cavity having an upper region with a first extraction opening formed therein for the raw mixture, wherein the raw mixture at said first extraction opening has been freed from at least one of the salts or the solid materials, said first extraction opening configured for supplying the raw mixture, which has been freed from at least one of the salts or the solid materials, to said catalytic converter; and
   said cavity having a lower region with a second extraction opening formed therein for a brine containing at least one of the salts or the solid materials, said second extraction opening is disposed lower down than said feed opening.

2. The combination according to claim 1, wherein said cavity is cylindrical and is vertically aligned, and said cavity has a diameter and a vertical length that is greater than said diameter.

3. The combination according to claim 1, wherein said first extraction opening is disposed in a region of a highest point of said cavity.

4. The combination according to claim 1, wherein said second extraction opening is disposed in a region of a lowest point of said cavity.

5. The combination according to claim 1, wherein said feed opening is disposed at a cavity-sided end of said rising pipe which protrudes vertically into said cavity.

6. The combination according to claim 1, further comprising at least one heating element located on at least one of said walls of said case.

7. The combination according to claim 1, wherein the pumpable aqueous fluid mixture lies substantially in a range of a critical point for the pumpable aqueous fluid mixture.

* * * * *